United States Patent [19]

Kadoya et al.

[11] Patent Number: 4,603,197

[45] Date of Patent: Jul. 29, 1986

[54] MANNOGLUCAN DERIVATIVES

[75] Inventors: Shizuo Kadoya; Kazuhiro Inoue; Morihiro Kohno; Hidemasa Ogawa, all of Tokyo, Japan

[73] Assignee: Daiichi Seiyaku Co., Ltd., Tokyo, Japan

[21] Appl. No.: 566,452

[22] Filed: Dec. 28, 1983

[30] Foreign Application Priority Data

Dec. 29, 1983 [JP] Japan ................................ 57-232684

[51] Int. Cl.$^4$ ............................................ C08B 37/00
[52] U.S. Cl. ...................................... 536/123; 536/1.1
[58] Field of Search ................. 536/1.1, 4.1, 123, 124; 424/180

[56] References Cited

U.S. PATENT DOCUMENTS 4,398,023 8/1983 Miyachi et al. ...................... 536/1.1

Primary Examiner—Johnnie R. Brown
Assistant Examiner—Elli Peselev
Attorney, Agent, or Firm—Sughrue, Mion, Zinn, Macpeak and Seas

[57] ABSTRACT

Mannoglucan derivatives wherein from about 2 to 51 per 100 of side chain α-D-mannopyranosyl residues of mannoglucan have been cleaved and reduced to polyhydroxy residues possess antitumor activity with reduced pyrogenecity.

7 Claims, No Drawings

MANNOGLUCAN DERIVATIVES

FIELD OF THE INVENTION

This invention relates to a novel mannoglucan derivative having antitumor activity.

BACKGROUND OF THE INVENTION

The present inventors previously discovered that *Microellobosporia grisea*, an actinomycete, produces a polysaccharide, D-manno-D-glucan (DH-6665F), having anti-tumor activity and succeeded in separating and purifying the same as disclosed in Japanese Patent Application (OPI) No. 155201/81 and reported in *Carbohydrate Research*, 114 (1983), 164–168 (Elsevier).

However, in some cases, D-manno-D-glucan (DH-6665F) (hereinafter referred to as "mannoglucan") caused side effects such as transient pyrexia.

SUMMARY OF THE INVENTION

As a result of further investigations, the present inventors have found that the pyranose rings of mannoglucan are partially cleaved with periodic acid or a salt thereof and that the resulting aldehyde groups are reduced to hydroxymethyl groups to give a mannoglucan derivative which does not possess the above described side effects and has enhanced antitumor activity over that of the original mannoglucan.

The present invention relates to mannoglucan derivatives having a basic repeating unit represented by the formula (I):

$$\begin{array}{c} X \\ \downarrow \\ \xrightarrow{\beta} 4G \xrightarrow{6} \xrightarrow{\beta} 4G \longrightarrow \\ 3 \\ \uparrow \\ Y \end{array} \quad (I)$$

wherein G represents a D-glucopyranosyl residue; X and Y each represents

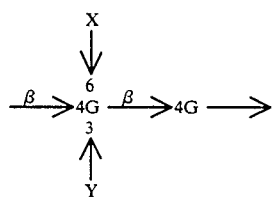

A or

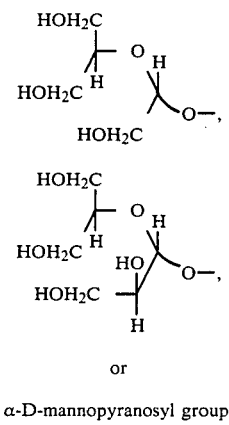

B

α-D-mannopyranosyl group;     M and the ratio of the total number of the groups A and B to the number of the group M, (A+B)/M, is in the range of from 2/98 to 51/49, and a process for preparing the same.

The mannoglucan derivatives of the present invention have molecular weight peaks of from 850,000±90,000 to 1,200,000±120,000 by gel-permeation chromatography with dextran as the standard; show elemental analysis values of C: 41 to 44%; H: 6 to 7%; and N: not more than 0.4%, and specific rotatory powers $[\alpha]_D^{25}$ (c=0.5, water) of from +15°±5° to +60°±10°; and are easily soluble in water, and sparingly soluble in methanol, ethanol, ethyl acetate, acetone and diethyl ether.

The mannoglucan derivatives of the present invention can be obtained by partial cleavage of the pyranose rings of mannoglucan with periodic acid or its salt, followed by borohydride reduction.

DETAILED DESCRIPTION OF THE INVENTION

The repeating unit represented by the formula (I) which appears throughout the specification and claims can be expressed by the following formula:

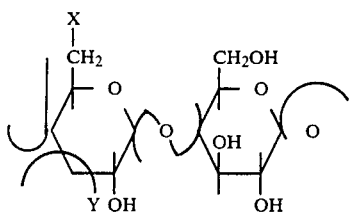

wherein X and Y are as defined above.

The process for producing the mannoglucan derivatives of the present invention is hereinafter described in detail.

An aqueous solution of periodic acid or a salt thereof, such as sodium periodate and potassium periodate, is added with stirring to a dilute aqueous solution of mannoglucan in a given molar ratio to sugar residue (molecular weight: 162). Thereafter, the reaction mixture is maintained at low temperatures of not more than about 15° C., preferably 10° C. or below, in the dark to complete the oxidation reaction. The reaction time is preferably 5 days or more since, for example, when mannoglucan is oxidized at 5° C. with 0.25 mol of sodium periodate, periodate ion disappears in 4 or 5 days. After completion of the oxidation, an amount of a reducing agent such as sodium borohydride in excess of that required to reduce the aldehyde groups is added to the reaction mixture, and the mixture is allowed to stand at a temperature of about 0° C. to about 50° C., preferably at room temperature for a period of more than about 2 hours to reduce the aldehyde groups to hydroxymethyl groups. The pH of the reaction mixture is adjusted to 3 to 6, preferably 5, with an organic or inorganic acid such as hydrochloric acid, sulfuric acid, formic acid or acetic acid to decompose the excess reducing agent. The mixture can then be subjected to dialysis against water, for example, deionized water, and the desalted nondialyzable solution is concentrated. Insoluble materials, if any, can be removed by centrifugation. The supernatant liquor is poured into two or three times volumes of an alcohol such as ethanol or acetone while stirring, and the resulting precipitate is collected, and, if necessary, washed with an alcohol, e.g., ethanol and then with acetone, and dried in vacuo to obtain a mannoglucan derivative. Instead of the above-described dialysis, the desalting can be carried out by, for example, a method in which a quaternary ammonium salt, such as cetylpyridinium chloride, and a borate such as borax are added to the mixture under an alkaline condition, for example, at a pH of 9 to 10, in order to precipitate the derivative as a cetylpyridiniumborate complex. The resulting complex is dissolved in a dilute organic or inorganic acid such as formic acid, acetic acid, hydrochloric acid or sulfuric acid and poured into an alcohol, e.g., ethanol, to obtain a desalted mannoglucan derivative similarly to the case of desalting by dialysis.

In the above-described oxidation reaction, derivatives having varying degrees of cleavage of the mannopyranose rings can be obtained by controlling the molar ratio of periodic acid or its salt to sugar residue. For instance, when the above-described molar ratios are 0.05, 0.10, 0.25, and 0.35, there are obtained mannoglucan derivatives each having a certain degree of cleavage. These respective derivatives are designated as PA-5, PA-10, PA-25, and PA-35, and their properties are described below in detail.

I. PHYSICOCHEMICAL PROPERTIES (1) Solubility

PA-5, PA-10, PA-25 and PA-35 are all easily soluble in water and sparingly soluble in organic solvents such as methanol, ethanol, ethyl acetate, acetone, diethyl ether, etc.

(2) Optical Rotation

Specific rotatory powers in a 0.5% aqueous solution $[\alpha]_D^{25}$ as measured with a Perkin-Elmer model 141 polarimeter are $+60°\pm10°$ for PA-5; $+51°\pm10°$ for PA-10; $+30°\pm5°$ for PA-25, and $+15°\pm5°$ for PA-35.

(3) Elemental Analysis (%)

|  | C | H | N |
|---|---|---|---|
| PA-5 | 41.9 | 6.1 | not more than 0.4 |
| PA-10 | 42.1 | 6.1 | not more than 0.4 |
| PA-25 | 42.4 | 6.4 | not more than 0.4 |
| PA-35 | 42.1 | 6.2 | not more than 0.4 |

(4) Molecular Weight

100 μl of a 0.5% aqueous solution of each test sample was injected into a G-5000 PW column (made by Toyo Soda Manufacturing Co., Ltd.) connected to an HLC-803D high performance liquid chromatograph (made by Toyo Soda Manufacturing Co., Ltd.) and a refractive-index detector. The column was eluted with a 0.1M potassium acetate buffer (pH 6.5) at a flow rate of 1 ml/min. Molecular weight was estimated with dextran T-500, T-70 and T-40 (made by Pharmacia Fine Chemicals Co.) as the standards. Molecular weights of elution peaks of PA-5, PA-10, PA-25 and PA-35 were 920,000±90,000, 1,050,000±100,000, 1,200,000±120,000, and 850,000±90,000, respectively.

(5) In order to elucidate the structures of the mannoglucan derivatives of the invention and mannoglucan, the following analyses were conducted.

(a) Each of PA-5, PA-10, PA-25, PA-35 and mannoglucan was completely hydrolyzed with 1N sulfuric acid at 100° C. for 6 hours in a sealed tube, and the products were analyzed as alditol acetates by gas chromatography in a usual manner to determine the constituting sugar ratios.

The results obtained are shown in Table 1.

TABLE 1

| | Constituting Sugar Ratio (molar ratio) | | |
|---|---|---|---|
| | Mannose/Glucose | Glycerol/Glucose | Erythritol/Glucose |
| PA-5 | 0.86 | 0.07 | <0.01 |
| PA-10 | 0.80 | 0.15 | <0.01 |
| PA-25 | 0.61 | 0.33 | <0.01 |
| PA-35 | 0.43 | 0.45 | 0.01 |
| Mannoglucan | 0.88 | 0 | 0 |

(b) Mannoglucan was completely methylated by the method of Hakomori, J. Biochem. (Tokyo), 55 (1964) 205, hydrolyzed with an acid, and the methylated products were analyzed as alditol acetates by gas chromatography in a usual manner. The results obtained are as shown in Table 2.

TABLE 2

| Methylation Analysis | |
|---|---|
| Alditol Acetate | Molar Ratio |
| 1.5-Di-O—acetyl-2,3,4,6-tetra-O—methyl-D-mannitol | 1.00 |
| 1,4,5-Tri-O—acetyl-2,3,6-tri-O—methyl-D-glucitol | 0.50 |
| 1,3,4,5,6-Penta-O—acetyl-2-O—methyl-D-glucitol | 0.47 |

(c) Results of complete Smith-degradation and controlled Smith-degradation of mannoglucan according to the procedure as reported in Inoue et al, *Carbohydrate Research*, 114 (1983), 245-256 are shown in Table 3.

TABLE 3

| | Smith-Degradation (molar ratio) | | |
|---|---|---|---|
| | Glycerol | Erythritol | Glucose |
| Complete-Degradation | 2.00 | 1.01 | 1.00 |
| Controlled-Degradation | 2.00 | 0.14 | 0.00 |

(d) In addition to glycerol (2.0 mol) and erythritol (0.14 mol) given in Table 3 above, 2-O-β-D-glucosyl-D-erythritol (0.74 mol) and 2,4-bis-hydroxymethyl-5-O-β-D-glucosyl-1,3-dioxane (0.35 mol) were obtained as the controlled Smith-degradation products of mannoglucan. Furthermore, acetolysis of mannoglucan gave 3-O-α-D-mannosyl-D-glucose and cellobiose, and partial acid hydrolysis of mannoglucan (0.33N sulfuric acid, 100° C., 7 hrs.) yielded 6-O-α-D-mannosyl-D-glucose and cellobiose.

From the foregoing analytical results, it is deduced that mannoglucan has the following main structure:

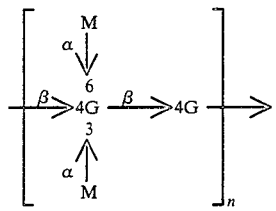

wherein G represents D-glucopyranosyl residue and M represents D-mannopyranosyl group, that is, mannoglucan has a tetrasaccharide repeating-unit structure, in that a single mannosyl group is located at both O-3 and O-6 of every other β-D-(1→4)-glucosyl residue, whereas the presence of erythritol in the controlled Smith-degradation products shows that a small proportion (14% in Table 3) of (1→4)-linked D-glucosyl residues may be present in the main chain as contiguous (1→4)-linked units, or in the side chains between "G" and "M", or both, as irregular (1→4)-linked glucosyl residues.

The analytical data shown in Table 1 indicate that in the mannoglucan derivatives, e.g., PA-5, PA-10, PA-25 and PA-35, the mannopyranosyl groups of mannoglucan are partially altered to polyhydroxy groups as groups A and B (see, Formula (I)) by periodate oxidation followed by borohydride reduction, whereas the glucopyranosyl residues are resistant to periodate oxidation. The ratios of the total number of the groups A and B to the number of the group M, i.e., (A+B)/M, in the respective mannoglucan derivatives were calculated from the analytical data (Table 1), based on the degradation of mannopyranosyl groups, as given in Table 4.

TABLE 4

| | Constituting Ratio in Side Chain (%) | |
|---|---|---|
| | A + B | M |
| PA-5 | 2 | 98 |
| PA-10 | 9 | 91 |
| PA-25 | 31 | 69 |
| PA-35 | 51 | 49 |

Thus, the mannoglucan derivatives of the present invention primarily consist of the repeating-unit structure represented by the formula (I), but it is also probable that the mannoglucan derivative of the present invention may contain a small proportion of the residue represented by the formula C below. That is, less than about 2% of the total amount of the every other (1→4)-linked glucosyl residue in the formula (I) (i.e., "-4G-") and the above-described irregular (1→4)-linked glucosyl residues may be converted into the group of the formula C.

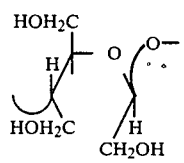
C:

In the formula (I), the ratio (A+B)/M preferably falls within the range of from 2/98 to 51/49 from the standpoint of side effects and antitumor activity.

II. BIOLOGICAL PROPERTIES

(1) PYROGENECITY

Pyrogen test was conducted for each of the mannoglucan derivatives in accordance with Japan Pharmacopeia (X), page 721, 1981. Each sample dissolved in a sterilized physiological saline solution (Japan Pharmacopeia) was administered to 3 rabbits per group each weighing about 2 Kg through the ear vein in an amount of 10 ml/Kg-body weight. Data for the increase in body temperature after the administration are tabulated in Table 5.

TABLE 5

| | | Increase of Body Temperature (°C.) | | | | |
|---|---|---|---|---|---|---|
| Sample | Dose (mg/10 ml/Kg) | Run Nos. 1 | 2 | 3 | Total | Judgement* |
| PA-5 | 0.20 | 0.45 | 0.35 | 0.35 | 1.15 | − |
| | 0.50 | 0.30 | 0.40 | 0.40 | 1.10 | − |
| PA-25 | 0.20 | 0.10 | 0.20 | 0.40 | 0.70 | − |
| | 0.50 | 0.20 | 0.35 | 0.25 | 0.80 | − |
| Mannoglucan | 0.04 | 0.70 | 0.65 | 0.25 | 1.60 | + |
| | 0.20 | 1.15 | 1.20 | 1.20 | 3.55 | + |

*Note:
−: negative
+: positive

The above results demonstrate that pyrogenecity of PA-5 and PA-25 was obviously more reduced than the original mannoglucan.

(2) Antitumor Activity (a) Effect on Allogeneic Ehrlich Tumor in Mice

Ehrlich carcinoma ($3 \times 10^6$ cells/mouse) was subcutaneously inoculated to the inguinal region of six ddY male mice per group. Each sample dissolved in a physiological saline solution was intraperitoneally administered once on day 12 and once on day 17. For comparison, mannoglucan was administered in the same manner. Thirty days after the tumor inoculation, the mice were killed and the tumors were extirpated and weighed. The antitumor effect was evaluated by comparing the average tumor weight of the treated group (T) with that of the untreated control group (C). The results obtained are shown in Table 6.

TABLE 6

| | Effect of Ehrlich Solid Tumor (i.p.) | |
|---|---|---|
| Sample | Dose (mg/Kg) | Tumor Weight Ratio T/C × 100 (%)[1] |
| PA-5 | 10 × 2 | 14.4 ± 9.0***[2] |
| | 100 × 2 | 5.8 ± 1.8*** |
| PA-10 | 10 × 2 | 26.7 ± 22.0* |
| | 100 × 2 | 14.1 ± 5.4*** |
| PA-25 | 10 × 2 | 30.3 ± 13.7** |
| | 100 × 2 | 4.0 ± 1.4*** |
| PA-35 | 10 × 2 | 31.0 ± 8.7** |
| | 100 × 2 | 55.2 ± 17.7 |
| Mannoglucan | 10 × 2 | 24.0 ± 10.2** |
| | 100 × 2 | 28.6 ± 9.9** |
| Control[3] | — | 100.0 ± 19.5 |

Note:
[1]Tumor weight of treated group/tumor weight of control group; mean ± S.E.
[2]Significant difference from the control group by Student's t-test:
*P < 0.05
**P < 0.01
***P < 0.001
[3]Tumor weight of the control group on day 30: 2.77 ± 0.40 (g)

(b) Effect on MM46 Syngeneic Tumor in Mice

MM46 mammary carcinoma ($4 \times 10^6$ cells/mouse) was subcutaneously implanted into the inguinal region of seven C3H/He male mice per group. Each sample dissolved in a physiological saline solution was subcutaneously administered into the back of the mice once on day 12 and once on day 17. For comparison, mannoglucan was administered in the same manner. On the 29th day from the tumor implantation, the antitumor effect was evaluated by the same method as described in (a) above.

TABLE 7

| | Effect on MM46 Solid Tumor (s.c.) | |
|---|---|---|
| Sample | Dose (mg/Kg) | Tumor Weight Ratio T/C × 100 (%)[1] |
| PA-5 | 10 × 2 | 59.8 ± 20.7 |

TABLE 7-continued

| | Effect on MM46 Solid Tumor (s.c.) | |
|---|---|---|
| Sample | Dose (mg/Kg) | Tumor Weight Ratio T/C × 100 (%)[1] |
| | 100 × 2 | 21.5 ± 7.4***[2] |
| PA-25 | 10 × 2 | 53.5 ± 14.1* |
| | 100 × 2 | 26.2 ± 10.2*** |
| Mannoglucan | 10 × 2 | 69.9 ± 19.9 |
| | 100 × 2 | 35.2 ± 11.7** |
| Control[3] | — | 100.0 ± 10.2 |

Note:
[1]Tumor weight of treated group/tumor weight of control group: mean ± S.E.
[2]Significant difference from the control group by Student's t-test:
*$P < 0.05$
**$P < 0.01$
***$P < 0.001$
[3]Tumor weight of the control group on day 30: 2.56 ± 0.26 (g)

As can be seen from the above results, it is obvious that PA-5, PA-10, PA-25 and PA-35 exhibit potent antitumor activity comparable or superior to that of the original mannoglucan.

Mannoglucan which is used in the preparation of the mannoglucan derivatives according to the present invention can be obtained by cultivation of *Microellobosporia grisea* as described before. Details of the preparation of mannoglucan are reported in *Carbohydrate Research*, 114 (1983), 164–168, published by Elsevier Science Publishers B.V., Amsterdam.

The mannoglucan derivative of the present invention can be suitably administered parenterally, for example, intravenous, intramuscular, subcutaneous or intratumor injection, generally at a dose of 2 to 200 mg per adult human, preferably 10 to 100 mg per adult human, once or twice a week. Of course, the above dose can be varied depending upon the body weight, route of administration, severity of conditions to be treated, times of administration per week, and the like. Also, the mannoglucan derivative of this invention can be administered in combination with other known chemotherapeutic agents, for example, 5-Fu, Mitomycin, etc. whereby increased antitumor effect can be expected.

The above injectable preparations can be prepared by dissolving the mannoglucan derivative of this invention in sterile water, physiological saline solution, Ringer's solution and the like which may contain other additives such as solubilizing agents, stabilizers and agents which make the solution isotonic. Further, the mannoglucan derivative can be a lyophilized preparation which is dissolved in an aqueous solvent of the above type just before the use. In preparing the lyophilized preparation, excipients such as mannitol, sorbintol, glucose, lactose, etc. can be added as excipients.

The present invention will now be illustrated in greater detail by way of Reference Example and Examples.

REFERENCE EXAMPLE

Preparation of Mannoglucan 100 ml of a medium (pH 7.0) consisting of 2% (w/v) of glucose, 0.5% (w/v) of peptone, 0.5% (w/v) of corn steep liquor, 0.3% (w/v) of yeast extract and 0.5% (w/v) of sodium chloride was prepared in a 500 ml flask and sterilized. One piece of agar slant of *Microellobosporia grisea* IFO 12518 obtained from the Institute for Fermentation, Osaka, Japan was inoculated into the medium and incubated for 5 days at 28° C. on a rotary shaker. 2 ml of the culture was again inoculated and incubated for 3 days at 28° C. in the same manner as described above. 200 ml of the resulting second seed culture was transferred to a 30 liter jar fermentor containing 20 liters of the same medium as used above and cultured for 66 hours at 28° C. under aeration (10 l/min.) and agitation (250 rpm) with an inner pressure of 0.5 Kg/cm$^2$. 20 liters of the third seed culture was transferred to a 1500 l jar fermentor containing 1000 liters of a medium (pH 7.2) consisting of 3.0% (w/v) of glucose, 2.0% (w/v) of corn steep liquor and 0.05% (w/v) of Adecanol LG 805 (made by Asahi Denka Kogyo K.K.) as an antifoaming agent and cultured for 88 hours at 28° C. under aeration of 500 l/min. with an inner pressure of 0.5 Kg/cm$^2$ and agitation at 165 rpm. After cultivation, the culture broth was heated for 30 minutes at 90° C., and cooled to room temperature. Radiolite #900 (made by Showa Kagaku Kogyo K.K.) was added to the broth, and insoluble materials were filtered off with a filter press and washed with water. The filtrate and washing were combined and passed through two columns (20 cm × 100 cm) each packed with 30 liters of Diaion PA306 (Cl$^-$), and the columns were washed with water. To the combined fluid (1200 liters) of the effluent and washing were added 25 liters of 10% cetylpyridinium chloride and 40 liters of a 0.5M borate buffer (pH 10), and the pH of the mixture was adjusted to 9. The resulting precipitate was collected and thoroughly washed with water. The precipitae was then dissolved in 100 liters of a 2% acetic acid solution, and then the solution was poured into 300 liters of ethanol. The resulting precipitate was collected, washed successively with aqueous 75% ethanol, ethanol and then acetone, and dried in vacuo to obtain 1.99 Kg of a white powder.

1.0 Kg of the powder thus obtained was dissolved in 70 liters of water, and the resulting solution was continuously centrifuged at 13,200×G for 5 minutes. The supernatant liquor was passed through a 0.45 μm membrane filter, and the filtrate was concentrated under reduced pressure to a volume of 25 liters. To the concentrate were added 75 liters of ethanol and 2 liters of ethanol saturated with sodium acetate. The resulting precipitate was collected and washed successively with aqueous 75% ethanol, ethanol and acetone, and dried in vacuo to obtain 910 g of mannoglucan as a white powder.

Elemental Analysis: C: 41.5%; H: 6.3%; N: not more than 0.4%

$[\alpha]_D^{25} = +65°$ (1% aqueous solution).

Glucose/Mannose (molar ratio) = 1.14.

EXAMPLE 1

5.0 g of mannoglucan was dissolved in 1.0 liter of deionized water and cooled to 5° C. 20 ml of a 1.65% aqueous solution of sodium periodate cooled to 5° C. was added to the solution while stirring, and the oxidation reaction was conducted for 14 days at 5° C. in the dark. The partially oxidized mannoglucan was then reduced with 0.5 g of sodium borohydride at room temperature for 20 hours. After decomposition of the excess of sodium borohydride by addition of acetic acid under cooling to a final pH of 5, the mixture was subjected to dialysis against deionized water. The nondialyzable solution was concentrated to a volume of about 400 ml, centrifuged at 9,000 rpm for 40 minutes, and the supernatant liquor was poured into 1.0 liter of ethanol while stirring. The resulting precipitate was collected, washed with ethanol and then with acetone, and dried in vacuo to obtain 4.8 g of PA-5 as a white powder.

EXAMPLE 2

The same procedure as described in Example 1 was used except for adding 40 ml of a 1.65% aqueous solution of sodium periodate for oxidation and 1.0 g of sodium borohydride for reduction to obtain 4.7 g of PA-10 as a white powder from 5.0 g of mannoglucan.

EXAMPLE 3

The same procedure as described in Example 1 was used except for adding 100 ml of a 1.65% aqueous solution of sodium periodate for oxidation and 2.5 g of sodium borohydride for reduction to obtain 4.7 g of PA-25 as a white powder from 5.0 g of mannoglucan.

EXAMPLE 4

The same procedure as described in Example 1 was used except for adding 140 ml of a 1.65% aqueous solution of sodium periodate for oxidation and 3.5 g of sodium borohydride for reduction to obtain 4.7 g of PA-35 as a white powder from 5.0 g of mannoglucan.

EXAMPLE 5

50.0 g of mannoglucan was dissolved in 10.0 liters of deionized water. After cooling to 5° C., 1.0 liter of a 1.65% aqueous solution of sodium periodate cooled to 5° C. was added to the solution, followed by allowing the mixture to stand at 5° C. for 6 days in the dark. The partially oxidized mannoglucan was then reduced with 25.0 g borohydride at room temperature for 20 hours. The excess of sodium borohydride was decomposed by addition of acetic acid under cooling to a final pH of 5. To the mixture were added 1.0 liter of a 10% aqueous solution of cetylpyridinium chloride and then 1.5 liters of a 0.5M borate buffer (pH 10). The resulting cetylpyridinium-borate complex of a mannoglucan derivative was collected, washed with deionized water, dissolved in 3.0 liters of a 2% aqueous solution of acetic acid under cooling and poured into 9.0 liters of ethanol while stirring. The precipitate thus formed was collected, washed with ethanol, and dissolved in 3.0 liters of deionized water, followed by filtration with a membrane filter (0.45 μm). 1.0 g of sodium acetate was dissolved in the filtrate, and the solution was poured into 9.0 liters of ethanol while stirring. The resulting precipitate was collected, washed successively with ethanol and acetone, and dried in vacuo to obtain 47.0 g of PA-25 as a white powder.

PREPARATION EXAMPLES

Formulation I

PA-25: 2 g
Sodium chloride: 9 g
Distilled water for injection to make total: 100 ml

Formulation II

PA-25: 2 g
Glucose: 50 g
Distilled water for injection to make total: 100 ml

Sodium chloride (9 g) or glucose (50 g) which makes the solution isotonic was dissolved in 80 ml of distilled water for injection and then PA-25 (2 g) was dissolved in the solution. An additional amount of distilled water for injection was added thereto to make the total volume 100 ml. The solution was filtered through a membrane filter (0.45 μm) and filed in ampoules in 1 ml portions, sealed and steam-sterilized under high pressure at 121° C. for 20 minutes to prepare injectable solutions each containing 20 mg of PA-25.

Formulation III

PA-25: 2 g
Sodium chloride: 9 g
Disodium phosphate: about 2 g
Citric acid: about 4 g
Distilled water for injection to make total: 100 ml Sodium chloride (9 g) was dissolved in distilled water for injection (80 ml). Disodium phosphate (about 2 g) and citric acid (about 4 g) were then dissolved therein to adjust the solution to a pH of 3 to 5 and PA-25 (2 g) was dissolved in the solution. An additional amount of distilled water for injection was then added thereto to make the total volume 100 ml. The solution was filtered through a membrane filter (0.45 μm) and filed in ampoules in 1 ml portions, sealed and steam-sterilized under high pressure at 121° C. for 20 minutes to prepare injectable solutions each containing 20 mg of PA-25.

Formulation IV

| | |
|---|---|
| PA-25 | 20 mg |
| D-mannitol | 500 mg |
| Dextran 40 | 40 mg |
| Total: | 560 mg (each vial) |

PA-25 (2 g), D-mannitol (50 g) and Dextran 40 (4 g) were dissolved in distilled water for injection to make the total volume 100 ml. The solution was filtered through a microbial membrane filter (0.2 μm), filled in 2 ml vials (1 ml solution in each vial), lyophilized and sealed to prepare lyophilized preparations each containing the above formulation.

While the invention has been described in detail and with reference to specific embodiments thereof, it will be apparent to one skilled in the art that various changes and modifications can be made therein without departing from the spirit and scope thereof.

What is claimed is:

1. A mannoglucan derivative comprising a basic repeating unit represented by the formula:

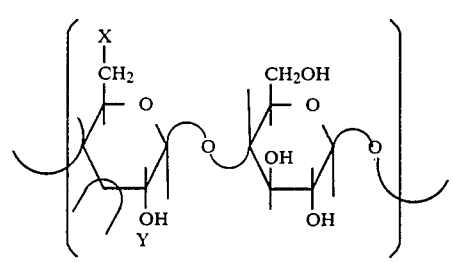

wherein X and Y each represent

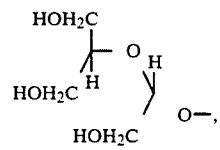

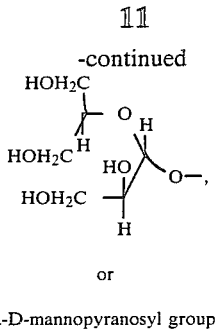 B or

α-D-mannopyranosyl group; M and the ratio of the total number of the groups A and B to the number of the group M, (A+B)/M, is in the range of from 2/98 to 51/49, wherein said mannoglucan derivative has a molecular weight peak of from 850,000±90,000 to 1,200,000±120,000, as determined by gel-permeation chromatography with dextran as a standard.

2. A mannoglucan derivative as claimed in claim 1, wherein up to 2% of the unsubstituted (1→4)-linked D-glucosyl residues are polyhydroxylated.

3. A mannoglucan derivative as claimed in claim 1 which shows elemental analysis values of C: 41 to 44%; H: 6 to 7%; and N: 0 to 0.4%, and a specific rotatory power $[\alpha]_D^{25}$ (c=0.5, water) of $+15°\pm5°$ to $60°\pm10°$, and is soluble in water and practically insoluble in methanol, ethanol, ethyl acetate, acetone and diethyl ether.

4. A mannoglucan derivative as claimed in claim 1, wherein the (A+B)/M ratio is 2/98, the molecular weight peak is 920,000±90,000, the elemental analysis values are C: 41.9%; H: 6.1%; and N: 0 to 0.4%, and the specific rotatory power $[\alpha]_D^{25}$ (c=0.5, water) is $+60°\pm10°$.

5. A mannoglucan derivative as claimed in claim 1, wherein the (A+B)/M ratio is 9/91, the molecular weight peak is 1,050,000±100,000, the elemental analysis values are C: 42.1%; H: 6.1%; and N: 0 to 0.4%, and the specific rotatory power $[\alpha]_D^{25}$ (c=0.5, water) is $+51°\pm10°$.

6. A mannoglucan derivative as claimed in claim 1, wherein the (A+B)/M ratio is 31/69, the molecular weight peak is 1,200,000±120,000, the elemental analysis values are C: 42.4%; H: 6.2%; and N: 0 to 0.4%, and the specific rotatory power $[\alpha]_D^{25}$ (c=0.5, water) is $+30°\pm5°$.

7. A mannoglucan derivative as claimed in claim 1, wherein the (A+B)/M ratio is 51/49, the molecular weight peak is 850,000+90,000, the elemental analysis values are C: 42.1%; H: 6.2%; and N: 0 to 0.4%, and the specific rotatory power $[\alpha]_D^{25}$ (c=0.5, water) is $+15°\pm5°$.

* * * * *